United States Patent [19]

Rothgery

[11] 4,228,290
[45] Oct. 14, 1980

[54] AMINO ESTER DERIVATIVES OF 3-TRIHALOMETHYL-1,2,4-THIADIAZOLES

[75] Inventor: Eugene F. Rothgery, North Branford, Conn.

[73] Assignee: Olin Corporation, New Haven, Conn.

[21] Appl. No.: 102,053

[22] Filed: Dec. 10, 1979

Related U.S. Application Data

[62] Division of Ser. No. 006,318, Jan. 25, 1979.

[51] Int. Cl.³ .................... A01N 43/80; C07D 285/08
[52] U.S. Cl. .................................................. 548/128
[58] Field of Search ........................................ 548/128

[56] References Cited

U.S. PATENT DOCUMENTS

| | | | |
|---|---|---|---|
| 3,260,725 | 7/1966 | Schroeder | 548/128 |
| 3,324,141 | 6/1967 | Bernstein | 548/128 |
| 3,573,317 | 3/1971 | Smith | 260/294.8 |
| 3,629,275 | 12/1971 | Metzger et al. | 548/128 |
| 3,673,203 | 6/1972 | Miller | 548/128 |
| 3,686,198 | 8/1972 | Metzger et al. | 548/128 |
| 3,720,684 | 3/1973 | Krenzer et al. | 548/128 |
| 3,764,685 | 10/1973 | Krenzer et al. | 424/270 |
| 3,822,280 | 7/1974 | Moser et al. | 548/128 |
| 3,873,299 | 3/1975 | Metzger et al. | 71/90 |
| 3,884,929 | 5/1975 | Smith | 548/128 |
| 3,917,478 | 11/1975 | Moser et al. | 71/90 |
| 4,107,377 | 8/1978 | Tobin | 548/128 |

*Primary Examiner*—Alton D. Rollins
*Attorney, Agent, or Firm*—William A. Simons; Thomas P. O'Day

[57] ABSTRACT

Disclosed are selected amino ester derivatives of 3-trihalomethyl-1,2,4-thiadiazole compounds of the formula:

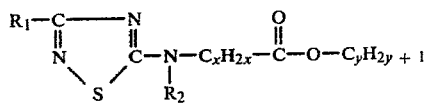

wherein $R_1$ is a $CCl_3$ or $CF_3$ group; $R_2$ is a hydrogen or a lower alkyl group of 1 to 4 carbon atoms; x is from 1 to 4; and y is from 1 to 5. These compounds are shown to have herbicidal properties.

5 Claims, No Drawings

AMINO ESTER DERIVATIVES OF 3-TRIHALOMETHYL-1,2,4-THIADIAZOLES

BACKGROUND OF THE INVENTION

1. Field of the Invention

This invention relates to selected amino ester derivatives of 3-trihalomethyl-1,2,4-thiadiazole compounds and their use as herbicides.

2. Description of the Prior Art

Various 3,5-substituted-1,2,4-thiadiazole compounds have been known to possess different types of pesticidal activities such as fungicidal, herbicidal, insecticidal, nematocidal and the like. For example, U.S. Pat. No. 3,629,275, which issued to Carl Metzger et al on Dec. 21, 1971, discloses certain carboxylic acid (1,2,4-thiadiazol-5-yl)-amides and their use as herbicides. These disclosed amide compounds differ from the compounds of the present invention by (1) having a 3-position substituent selected from a lower alkyl group or phenyl group (instead of a trihalomethyl group) and (2) having as a 5-position group a carboxylic acid amide (instead of the present amino ester derivatives described below).

BRIEF SUMMARY OF THE INVENTION

Accordingly, the present invention is directed to, as compositions of matter, selected amino ester derivatives of 3-trihalomethyl-1,2,4-thiadiazole compounds of the formula:

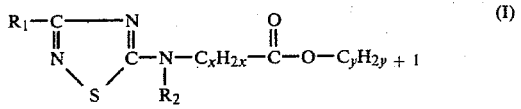

wherein $R_1$ is a $CCl_3$ or $CF_3$ group; $R_2$ is hydrogen or a lower alkyl group having 1 to 4 carbon atoms; x is from 1 to 4; and y is from 1 to 5. The present invention also covers the use of these compounds as herbicides.

DETAILED DESCRIPTION

The amino ester derivatives of the present invention may be prepared by reacting the corresponding 5-chloro-3-trihalomethyl-1,2,4-thiadiazole with a hydrochloride salt of the desired amino acid ester which will form the 5-position substituent of the product, preferably in the presence of a base such as triethylamine or sodium carbonate. This general reaction is illustrated in Equation (A), below, wherein 5-chloro-3-trichloromethyl-1,2,4-thiadiazole is reacted with ethyl glycinate hydrochloride to make 5-(ethyl glycinato)-3-trichloromethyl-1,2,4-thiadiazole:

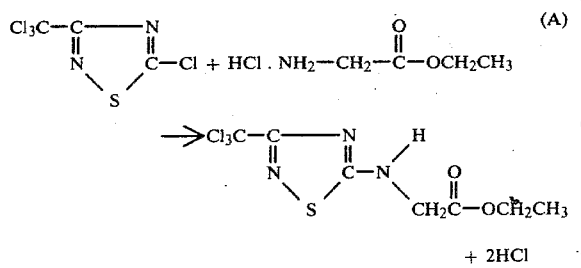

Suitable 5-chloro-3-trihalomethyl-1,2,4-thiadiazole reactants include 5-chloro-3-trichloromethyl-1,2,4-thiadiazole and 5-chloro-3-trifluoromethyl-1,2,4-thiadiazole. 3-Chloro-5-trichloromethyl-1,2,4-thiadiazole is described in U.S. Pat. No. 3,260,725, which issued to H. A. Schroeder on July 12, 1966, and is made by reacting trichloromethylacetamidine or its hydrochloride with trichloromethanesulfenyl chloride in the presence of alkali. 3-Chloro-5-trifluoromethyl-1,2,4-thiadiazole is described in the following article, H. A. Schroeder, *Journal Organic Chemistry*, 27, 2589 (1962) and is prepared by the side-chain fluorination of 5-chloro-3-trichloromethyl-1,2,4-thiadiazole with Swart's fluorination mixture consisting of antimony fluoride, antimony trichloride and chlorine.

Suitable amino acid ester reactants include the hydrochloride salts of ethyl glycinate, ethyl betaalanate and ethyl sarcosinate. All three of these named esters are reported in the literature. Ethyl glycinate is prepared by the Fischer esterification of glycine in ethanol. The other two named amino acid esters are prepared similarly.

Any conventional reaction conditions may be employed in the synthesis of the present compounds and the present invention is not intended to be limited to any particular reaction conditions. Advantageously and preferably, the reaction is carried out with equimolar quantities of the above two reactants and in the presence of a suitable inert hydrocarbon solvent. Ethanol is the preferred solvent, but other inert solvents may be used. The reaction temperature and time will both depend upon the exact reactants being employed, but in most situations, reaction temperatures from about 0° C. to about 130° C. and reaction times from about 1 hour to about 30 hours are preferred. The desired product may be recovered from the reaction mixture by any conventional means, for example, ether extraction, distillation and the like. Finally, it should be noted that while the reaction illustrated by Equation (A) is a preferred method of preparing compounds of the present invention, other synthesis methods may also be employed.

In accordance with the present invention, it has been found that compounds of Formula (I), above, may be used for defoliation or for desiccation of the green parts of plants. They are, in particular, suitable singly, or in mixtures thereof, for the control of weeds. As contemplated herein, the term "weeds" is meant to include not only weeds in the narrow sense, but also in the broad sense, whereby to cover all plants and vegetation considered undesirable for the particular purposes in question. Whether the active compounds according to the present invention act as total or selective herbicides depends essentially on the amount applied, as the artisan will appreciate.

Specifically, in practicing the process of the present invention, undesirable plant and vegetation are contacted with a herbicidally effective amount of the above-mentioned compounds. It is to be understood that the term "herbicidally effective amount" as used in the specification and claims herein is intended to include any amount that will kill or control said undesirable plants and vegetation when either employed by itself (i.e., in full concentration) or in sufficient concentration with a carrier or other substance. Of course, this amount may be constantly changing because of the possible variations in many parameters. Some of these may include: the number and type of plants to be controlled or killed; the type of loci or media to which the present compounds can be applied (e.g., weeds within crop areas, fence lines); degree of effectiveness required; and type of carrier, if any. The step of contacting may be accomplished by applying the present active compounds to the undesirable plants themselves or to the immediate locus or ground surrounding said plants. For most situations, the application of the compounds of the present invention in amounts from about 0.1 pound per acre to about 10 pounds per acre will be sufficient for selective or total herbicidal effect.

The above-mentioned compounds of the present invention may be formulated and applied to any conventional methods that include using the compounds alone or with a carrier or other substances which may enhance the effectiveness of the chemical or facilitate handling. Moreover, the activity of the present compounds may be broadened by the addition thereto of other known biocides.

Specific methods of formulating and applying these active compounds include applying them in the form of dusts, dust or emulsion concentrates, wettable powders, and concentrates, granulates, dispersions, sprays, solutions and the like.

The dusts and dust concentrates are usually prepared by simply grinding together the active compounds of the present invention with a finely divided inert diluent such as walnut flour, diatomaceous earth, fuller's earth, attaclay, talc or kaolin. Dusts generally contain from about 1% to about 15% by weight of active compound and dust concentrates usually contain from about 16% to about 75% by weight active compound. In practice, dust concentrates are usually admixed with more inert diluent at the site of use to form dusts before being applied to undesirable plant foliage.

Wettable powders are generally prepared in the same manner as dust concentrates, but usually about 1% to 10% by weight of a dispersing agent, for example, an alkali metal lignosulfonate and about 1% to 10% of a surfactant, such as a non-ionic surfactant, are incorporated in the formulation. For most applications, the wettable powder is usually dispersed in water and applied as a spray.

Emulsifiable liquids may be prepared by dissolving the active compound in an organic solvent, such as xylene or acetone, and admixing the thus formed solution with a surfactant or an emulsifier. The emulsified liquid is then generally dispersed in water for spray application.

It is possible to formulate granulates whereby these active compounds are dissolved in an organic solvent and the resulting solution is then applied to a granulated mineral or the like (e.g., bentonite, $SiO_2$, or the like) followed by evaporating off the organic solvent. Granulates can also be obtained by the compacting of the carrier material with the active substance and then reducing this compacted material in size.

Furthermore, the applied formulations of the present invention include other liquid preparations such as dispersions, sprays or solutions. For these purposes, one of the above-mentioned active compounds, or more than one active compound, is normally dissolved in a suitable organic solvent, solvent mixtures or water. As organic solvents, it is possible to use any suitable aliphatic and aromatic hydrocarbon or their derivatives. It is preferred that the solvent be odorless and, moreover, be inert to the active compound.

It should be clearly understood that such herbicide formulations, the ingredients which may make up such formulations other than the active compounds and the dosages, and means of applying these formulations may include all known and conventional substances, amounts and means, respectively, that are suitable for obtaining the desired herbicidal result. And, therefore, such process parameters are not critical to the present invention.

The following examples further illustrate the present invention. All parts and percentages employed therein are by weight unless otherwise indicated.

EXAMPLE 1

Preparation of 5-(Ethyl Glycinato)-3-Trichloromethyl-1,2,4-Thiadiazole 24 grams (0.1 mole) of 5-chloro-3-trichloromethyl-1,2,4-thiadiazole and 14 grams (0.1 mole) of ethyl glycinate hydrochloride were mixed in 350 milliliters of ethanol with 23 grams (0.21 mole) of triethylamine. The mixture was refluxed for one hour, then the solvent removed under vacuum. The resulting solids were extracted with ethyl ether. Removal of the ether left 26 grams of crude product. Recrystallization from carbon tetrachloride gave a product melting 68°–70° C. Elemental and infra-red analyses confirmed the material as 5-(ethyl glycinato)-3-trichloromethyl-1,2,4-thiadiazole.

EXAMPLE 2

Preparation of 5-(Ethyl Alanato)-3-Trichloromethyl-1,2,4-Thiadiazole 24 grams (0.1 mole) of 5-chloro-3-trichloromethyl-1,2,4-thiadiazole and 15.4 grams (0.1 mole) of ethyl betaalanate hydrochloride were mixed in 200 milliliters of ethanol. To this was added 21 grams (0.2 mole) of triethylamine and the mixture refluxed two hours. Removal of the solvent under vacuum left a white solid which was then extracted with hot carbon tetrachloride. This solution was reduced in volume and cooled to give 20.5 grams of product melting at 77°–79° C. Recrystallization from ethyl ether/ligroin raised the melting point to 100° C. Elemental and infra-red analyses confirmed the product as 5-(ethyl alanato)-3-trichloromethyl-1,2,4-thiadiazole.

EXAMPLE 3

Preparation of 5-(Ethyl Sarcosinato)-3-Trichloromethyl-1,2,4-Thiadiazole 24 grams (0.1 mole) of 5-chloro-3-trichloromethyl-1,2,4-thiadiazole and 15.4 grams (0.1 mole) of ethyl sarcosinate hydrochloride were mixed in 200 milliliters of ethanol. To this was added 21 grams (0.2 mole) of triethylamine and the mixture heated at 60° C. for two hours. The reaction mixture was poured into water, causing the product to separate as a heavier liquid. The product was extracted with ethyl ether and dried over magnesium sulfate. Addition of ligroin caused the product to separate again. The ether was decanted and the oily product placed under vacuum to yield 10.5 grams. Elemental and infra-red analyses confirmed the product as 5-(ethyl sarcosinato)-3-trichloromethyl-1,2,4-thiadiazole.

EXAMPLE 4

Preparation of 5-(Ethyl Glycinato)-3-Trifluoromethyl-1,2,4-Thiadiazole 19 grams (0.1 mole) of 5-chloro-3-trifluoromethyl-1,2,4-thiadiazole and 14 grams (0.1 mole) of ethyl glycinate hydrochloride were mixed in 200 milliliters of ethanol. To this was added 21 grams (0.2 mole) of triethylamine and the mixture heated one hour at 55° C.

The solvent was removed under vacuum and the product extracted with hot ether. Addition of ligroin and cooling gave the crude product. Recrystallization from carbon tetrachloride gave 14.2 grams of white solid, melting 55°–56° C. Elemental and infra-red analyses confirmed the product to be 5-(ethyl glycinato)-3-trifluoromethyl-1,2,4-thiadiazole.

Herbicide Screen

The active material made in Example 1 was tested for activity as effective herbicides by the following method.

A uniform aqueous dispersion of the chemical was made by dissolving the chemical in a solution of acetone containing a non-ionic surfactant in a concentration of 500 ppm. The resulting solution was diluted with water (1:9) to obtain a mixture of 10% acetone, 50 ppm surfactant, 0.208% test candidate made according to the above Example 1, and the balance water; 50 milliliters of this solution applied to a flat of 144 square inches corresponds to 10 lbs/acre. If further dilutions were required for testing at lower concentrations, water was added to this stock solution and the surfactant maintained at 50 ppm.

The aqueous solutions containing such chemical were applied to flats seeded with representative monocotyledonous and dicotyledonous plants. The test chemical was applied to one such flat immediately after it was seeded (pre-emergence screening) and to the other flat after the first true plant leaves had developed (post-emergence screening). Response was rated 12 to 21 days after treatment on a scale of 0 to 10, where 0 represents no injury and 10 represents complete kill. Table I, below, shows the results of this testing.

The crops and weeds used for the determination of activity were: Foxtail Millet (*Setaria italica*), Japanese Millet (*Echinochloa crusgalli*), Crabgrass (*Digitaria sanguinalis*), Wild Oats (*Avena fatua*), Morning Glory (*Ipomoea purpurea*), Mustard (*Brassica nigra*), Pigweed (*Amaranthus retroflexus*), Sesbania (*Sesbania exaltata*), Velvet Leaf (*Abutilon theophrasti*), Soybean (*Glycine max*), Cotton (*Gossypium hirsutum*), and Tomato (*Lycopersicon esculentum*).

TABLE I

| General Herbicide Activity at 10 lb/acre[1] | | | | | | | | | | | |
|---|---|---|---|---|---|---|---|---|---|---|---|
| CROPS | | | GRASSES | | | | BROAD-LEAF WEEDS | | | | |
| Soybean | Cotton | Tomato | Foxtail Millet | Japanese Millet | Crabgrass | Wild Oats | Morning Glory | Mustard | Pigweed | Sesbania | Velvet Leaf |
| 4F 6EF | 1F 5EF | 5F 6EF | 2 7 | 2F 3F | 1 9 | 0 4 | 4F 8 | 2F 5E | 2F 9 | 0 5EF | 0 5EF |

E = epinastic effects
F = formative effects
[1]The left side of the column shows the pre-emergence rating; the right side of the column shows the post-emergence rating.

What is claimed is:

1. A compound of the formula $$R_1-C=N \atop N\diagdown S \diagup C-N(R_2)-C_xH_{2x}-C(=O)-O-C_yH_{2y+1}$$

wherein $R_1$ is a $CCl_3$ or $CF_3$ group; $R_2$ is a hydrogen or a lower alkyl group of 1 to 4 carbon atoms; x is from 1 to 4; and y is from 1 to 5.

2. A compound of claim 1 having the formula $$Cl_3C-C=N \atop N\diagdown S \diagup C-N(H)-CH_2C(=O)-OCH_2CH_3$$

3. A compound of claim 1 having the formula $$Cl_3C-C=N \atop N\diagdown S \diagup C-N(H)-CH(CH_3)-C(=O)-O-CH_2CH_3$$

4. A compound of claim 1 having the formula $$Cl_3C-C=N \atop N\diagdown S \diagup C-N(CH_3)-CH_2-C(=O)-O-CH_2CH_3$$

5. A compound of claim 1 having the formula $$F_3C-C=N \atop N\diagdown S \diagup C-N(H)-CH_2C(=O)-O-CH_2CH_3$$

* * * * *

UNITED STATES PATENT AND TRADEMARK OFFICE
CERTIFICATE OF CORRECTION

PATENT NO. : 4,228,290
DATED : October 14, 1980
INVENTOR(S) : Eugene F. Rothgery It is certified that error appears in the above-identified patent and that said Letters Patent are hereby corrected as shown below:

In Column 1, before the heading entitled "BACKGROUND OF THE INVENTION", insert the following paragraph;

--This is a division, of application Serial No. 6,318, filed January 25, 1979.--

In Column 5, line 39, delete "such" and insert --each--.

Signed and Sealed this

Sixth Day of January 1981

[SEAL]

Attest:

Attesting Officer

SIDNEY A. DIAMOND

*Commissioner of Patents and Trademarks*